(12) United States Patent
Kim et al.

(10) Patent No.: US 6,322,805 B1
(45) Date of Patent: Nov. 27, 2001

(54) BIODEGRADABLE POLYMERIC MICELLE-TYPE DRUG COMPOSITION AND METHOD FOR THE PREPARATION THEREOF

(75) Inventors: Sung-Chul Kim, Taejeon; Eun-Ok Chang, Daejeon; In-Suk Song; Chaul-Min Pai, both of Taejeon, all of (KR)

(73) Assignee: Samyang Corporation, Seoul (KR)

( * ) Notice: Subject to any disclaimer, the term of this patent is extended or adjusted under 35 U.S.C. 154(b) by 0 days.

(21) Appl. No.: 09/547,545

(22) Filed: Apr. 12, 2000

Related U.S. Application Data (6362) Continuation-in-part of application No. 09/043,036, filed as application No. PCT/KR96/00163 on Sep. 21, 1996, now abandoned.

(30) Foreign Application Priority Data

Sep. 21, 1995 (KR) ................................. 95-30981

(51) Int. Cl.$^7$ ................. A61F 2/00; A61K 9/14
(52) U.S. Cl. ................. 424/426; 424/426; 424/486
(58) Field of Search ................. 424/426, 486

(56) References Cited

U.S. PATENT DOCUMENTS

| | | |
|---|---|---|
| 4,745,160 | 5/1988 | Churchill et al. . |
| 4,877,606 | 10/1989 | Churchill et al. . |
| 5,384,333 | 1/1995 | Davis et al. . |
| 5,412,072 | 5/1995 | Sakurai et al. . |
| 5,429,826 | 7/1995 | Nair et al. . |
| 5,449,513 | 9/1995 | Yokoyama et al. . |
| 5,510,103 | 4/1996 | Yokoyama et al. . |
| 5,543,158 | 8/1996 | Gref et al. . |
| 5,683,723 | 11/1997 | Spenlehauer et al. . |
| 5,702,717 | 12/1997 | Cha et al. . |
| 5,770,559 | 6/1998 | Manning et al. . |
| 5,780,044 | 7/1998 | Yewey et al. . |

FOREIGN PATENT DOCUMENTS

| | | |
|---|---|---|
| 0 397 307 | 3/1990 | (EP) . |
| 0 520 888 A1 | 6/1992 | (EP) . |
| 0552 802 A2 | 1/1993 | (EP) . |
| 0 583 955 A2 | 8/1993 | (EP) . |
| 9324154 | * 9/1993 | (WO) . |

OTHER PUBLICATIONS

Cavallaro, Viscosimetric Investigation of the Interaction Between Sodium Dodecylsulfate Micelles and a Polymer Drug Carrier, *International Journal of Pharmaceuticals*, 90(1993) 195–201.

Kataoka, Block Copolymer Micelle as Vehicles for Drug Delivery, *Journal of Controlled Release*, 24 (1993) 119–132.

(List continued on next page.)

*Primary Examiner*—Thurman K. Page
*Assistant Examiner*—Humera N. Sheikh
(74) *Attorney, Agent, or Firm*—Thorpe North & Western

(57) ABSTRACT

A biodegradable polymeric drug carrier micelle composition capable of solubilizing a hydrophobic drug in a hydrophilic environment comprises a biodegradable polymeric drug carrier micelle and a hydrophobic drug wherein the drug is physically trapped within and not covalently bonded to the polymeric drug carrier micelle. The drug carrying micelle is capable of dissolving in water to form a solution thereof, and the drug carrier comprises an amphiphilic block copolymer having a hydrophilic poly(alkylene oxide) component, and a biodegradable hydrophobic polymer component selected from the group consisting of poly(lactic acid), poly(glycoloc acid), poly(lactic-co-glycolic acid), poly($\epsilon$-caprolactone), a derivative thereof and a mixture thereof. Preferably the amphiphilic block copolymer has a molecular weight in a range of about 1430 to about 6000 Daltons and the hydrophilic component content is in a range of about 50 wt % to about 70 wt % based on the total weight of the block copolymer.

47 Claims, 4 Drawing Sheets

OTHER PUBLICATIONS

G. Kwon, Enhanced Tumor Accumulation and Prolonged Circulation Times of Micelle–forming Poly(ethylene oxide–aspartate) block Copolymer–adriamycin Conjugates, *Journal of Controlled Release,* 29 (1994) 17–23.

E. Piskin, Novel PDLLA/PEG Copolymer Micelles as Drug Carriers, *Journal of Biomaterial Science, Polymer Edition,* vol. 7, No. 4 pp. 359–373 (1995).

Glen S. Kwon, Block Copolymer Micelles as Long–Circulation Drug Vehicles, *Advanced Drug Delivery Reviews,* 16 (1995) 295–309.

Xichen Zhang, Development of Amphiphilic Diblock Copolymers as Miceller Carriers of Taxol, *International Journal of Pharmaceutics* 132 (1996) 195–206.

G. Kwon, Block Copolymer Micelles for Drug Delivery: Loading and Release of Doxorubicin, *Journal of Controlled Release* 48 (1997) 195–201.

So Yeon Kim, Methoxy Poly(ehtylene glycol) and E–caprolactone Amphiphilic Block Copolymeric Micelle Containing Indomethacin. II. Micelle Formation and Drug Release Behaviours, *Journal of Controlled Release,* 51, (1998) 13–22.

So Yeon Kim, Preparation and Characterization of Biodegradable Nanospheres Composed of Methoxy Poly(ethylene Glycol) and DL–lactide Block Copolymer as Novel Drug Carriers, *Jounral of Controlled Release,* 56 (1998) 197–208.

\* cited by examiner

BIODEGRADABLE POLYMERIC MICELLE-TYPE DRUG COMPOSITION AND METHOD FOR THE PREPARATION THEREOF

RELATED APPLICATIONS

This is a continuation-in-part patent application of pending U.S. patent application Ser. No. 09/043,036 filed Mar. 9, 1998, now abandonded which is based on PCT/KR96/00163, International Filing Date Sep. 21, 1996, which claims priority to Sep. 21, 1995.

FIELD OF THE INVENTION

The present invention relates to a biodegradable polymeric micelle-type drug composition, containing a water-soluble amphiphilic block copolymer micelle having a hydrophilic poly(alkylene oxide) component and a hydrophobic biodegradable component, and a hydrophobic drug physically trapped in the micelle. This micelle-type composition, enveloping a hydrophobic drug, can solubilize the hydrophobic drug in a hydrophilic environment to form a solution.

BACKGROUND OF THE INVENTION

Many important drugs are hydrophobic and have limited solubilities in water. In order to attain the expected therapeutic effect of such drug, it is usually required that a solubilized form of the drug be administered to a patient.

For this purpose, there have been developed a number of methods, which are based on the use of: auxiliary solvents; surfactants; soluble forms of the drug, e.g., salts and solvates; chemically modified forms of the drug, e.g., prodrugs; soluble polymer-drug complexes; special drug carriers such as liposomes; and others. Each of the above methods is hampered by one or more particular problems, e.g., the method based on the use of surfactant micelles to solubilize hydrophobic drugs has problems in that most of the surfactants are relatively toxic and that precipitation of hydrophobic drugs occurs when subjected to dilution.

The use of amphiphilic block copolymer micelles has recently been attracting much interest as a potentially effective drug carrier which is capable of solubilizing a hydrophobic drug in an aqueous environment. For example, there have been reported many studies on amphiphilic block copolymer micelles having surfactant-like properties, and particularly noteworthy are the attempts to incorporate hydrophobic drugs into block copolymer micelles stabilized due to the specific nature and properties of the copolymer. For example, EP No. 0 397 307 A2 discloses polymeric micelles of an AB type amphiphilic diblock copolymer which contains poly(ethylene oxide) as the hydrophilic component and poly(amino acids) as the hydrophobic component, wherein therapeutically active agents are chemically bonded to the hydrophobic component of the polymer. Although this polymeric micelle is provided as a means of administering a hydrophobic drug, it is disadvantageous in that it requires the introduction of functional groups into the block copolymer. EP No. 0 583 955 A2, on the other hand, discloses a method for physically incorporating hydrophobic drugs into amphiphilic diblock copolymer micelles described in EP No. 0 397 307 A2. This method, thus, solves the above disadvantage of the chemical bond type polymeric micelle drug. However, the poly(amino acid) segment may induce an immunoreaction and the use of an organic solvent in the preparation of the formulation may pose a problem. Furthermore, because the peptide bonds are cleaved by enzymes in the body, it is difficult to control the release rate of the drug incorporated therein.

EP No. 0 552 802 A2 discloses formation of chemically fixed micelles having poly(ethylene oxide) as the hydrophilic component and poly(lactic acid) as the hydrophobic component which can be crosslinked in an aqueous phase. That is, chemically fixed micelles are prepared by chemically crosslinking the hydrophobic component that constitutes the core, so as to mimic stabilized polymeric micelles. However, a crosslinking agent, or other means such as UV and heating with or without added peroxides, must be used in order to introduce crosslinking to the hydrophobic component of the block copolymer. Moreover, the biocompatibility or safety of such crosslinked polymer particles has yet to be established.

U.S. Pat. No. 4,745,160 discloses a pharmaceutically or veterinary acceptable amphiphilic, non-cross linked linear, branched or graft block copolymer having polyethylene glycol as the hydrophilic component and poly(D-, L- and DL-lactic acids) as the hydrophobic components. Although the block copolymer is an effective dispersing agent or suspending agent for a hydrophobic drug, the block copolymer has a molecular weight of 5,000 or more and is insoluble in water. Further, the hydrophilic component is at least 50 wt % based on the weight of the block copolymer and the molecular weight of the hydrophobic component is 5,000 or less. In the preparation process, a water-miscible and lyophilizable organic solvent is used. When a mixture of the polymer, drug and organic solvent is mixed with water, precipitates are formed and then the mixture is directly lyophilized to form particles. Therefore, when this particle is dispersed in water, it forms a colloidal suspension containing fine particles wherein hydrophilic components and hydrophobic components are mixed.

U.S. Pat. No. 5,543,158 discloses nanoparticle or microparticle formed of a block copolymer consisting essentially of poly(alkylene glycol) and a biodegradable polymer, poly (lactic acid). In the nanoparticle or microparticle, the biodegradable moieties of the copolymer are in the core of the nanoparticle or microparticle and the poly(alkylene glycol) moieties are on the surface of the nanoparticle or microparticle in an amount effective to decrease uptake of the nanoparticle or microparticle by the reticuloendothelial system. In this patent, the molecular weight of the block copolymer is too high to be soluble in water, and a nanoparticle is prepared by dissolving the block copolymer and a drug in an organic solvent, forming an o/w emulsion by sonication or stirring, and then collecting the precipitated nanoparticles containing the drug. It does not provide the concept of solubilization of hydrophobic drugs. The nanoparticles prepared in this patent are fine particles that are dispersed in water.

EP 0,520,888 A1 discloses a nanoparticle made of a poly(lactic acid) and poly(alkylene oxide) block copolymer. A high molecular weight poly(lactic acid) is used and a surfactant is employed in preparing a colloidal suspension of the nanoparticles. In this patent, nanoparticles are prepared by dissolving the block copolymer and a drug in an organic solvent, emulsifying the organic solution in water, and evaporating the organic solvent to precipitate the nanoparticles containing the drug. The resulting nanoparticles are fine particles having both hydrophilic and hydrophobic components and they are not soluble in water. The above patent does not disclose the concept of solubilization of hydrophobic drugs when the nanoparticles are dispersed in water. Hitherto, there has been no serious effort to solubilize hydrophobic drugs in water by way of using a water soluble micelle, in which the inner core of the micelle can physically trap such drugs.

Accordingly, the present inventors have endeavored to develop an improved water soluble solubilizer which is free of the problems mentioned above, and it has been unexpectedly found that an amphiphilic block copolymer micelle composed of a poly(ethylene oxide) hydrophilic component covering the surface of a hydrophobic core component made of poly(lactic acid), poly(lactic-co-glycolic acid), poly (glycolic acid), poly(ε-caprolactone) or a mixture thereof, is very effective in solubilizing hydrophobic drugs by physically incorporating them therewithin.

The resulting biodegradable polymeric micelle is water soluble and it is an effective solubilizing agent for a hydrophobic drug. The resulting composition is a solution of the hydrophobic drug carrying micelles and it is suitable for sustained release of the drug in vivo, thereby enhancing the therapeutic effect of the drug. Such effect may be maximized by controlling the molecular weights and the relative ratios of the hydrophilic and hydrophobic blocks.

SUMMARY OF THE INVENTION

Accordingly, it is an object of the present invention to provide a biodegradable polymeric micelle-type composition capable of solubilizing a hydrophobic drug in a hydrophilic environment which may be used in preparing a pharmaceutically effective solution of a hydrophobic drug.

Another object of the present invention is to provide a method for effectively solubilizing a hydrophobic drug in a hydrophilic environment and a method for effectively administering a hydrophobic drug to warm blooded animals by a means selected from the group consisting of oral, parenteral, topical, transdermal and transmucosal administration.

These and other objects are accomplished by the present invention which provides a biodegradable polymeric micelle-type drug composition which comprises: a biodegradable polymeric drug carrier micelle having a hydrophobic drug physically trapped within and not covalently bonded to a drug carrier micelle wherein the micelle is capable of dissolving in water to form a solution thereof. The drug carrier micelle comprises an amphiphilic block copolymer having a hydrophilic poly(alkylene oxide) component, and a biodegradable hydrophobic polymer component selected from the group consisting of poly(lactic acid), poly(glycolic acid), poly(lactic-co-glycolic acid), poly(ε-caprolactone). The amphiphilic block copolymer has a molecular weight in a range of about 1430 to about 6000 Daltons and the hydrophilic component content is in a range of about 50 wt % to about 70 wt % based on the total weight of the block copolymer.

The amphiphilic block copolymer micelle composition of the present invention is very effective in solubilizing hydrophobic drugs by way of physically incorporating them within the micelle. The resulting biodegradable polymeric micelle composition containing the solubilized hydrophobic drug is soluble in water to form a solution and it is suitable for sustained-release of the drug in vivo, thereby enhancing the therapeutic effect of the drug. Such therapeutic effect may be maximized by controlling the molecular weights and the relative ratios of the hydrophilic and hydrophobic blocks.

DETAILED DESCRIPTION OF THE INVENTION

Figure 1:
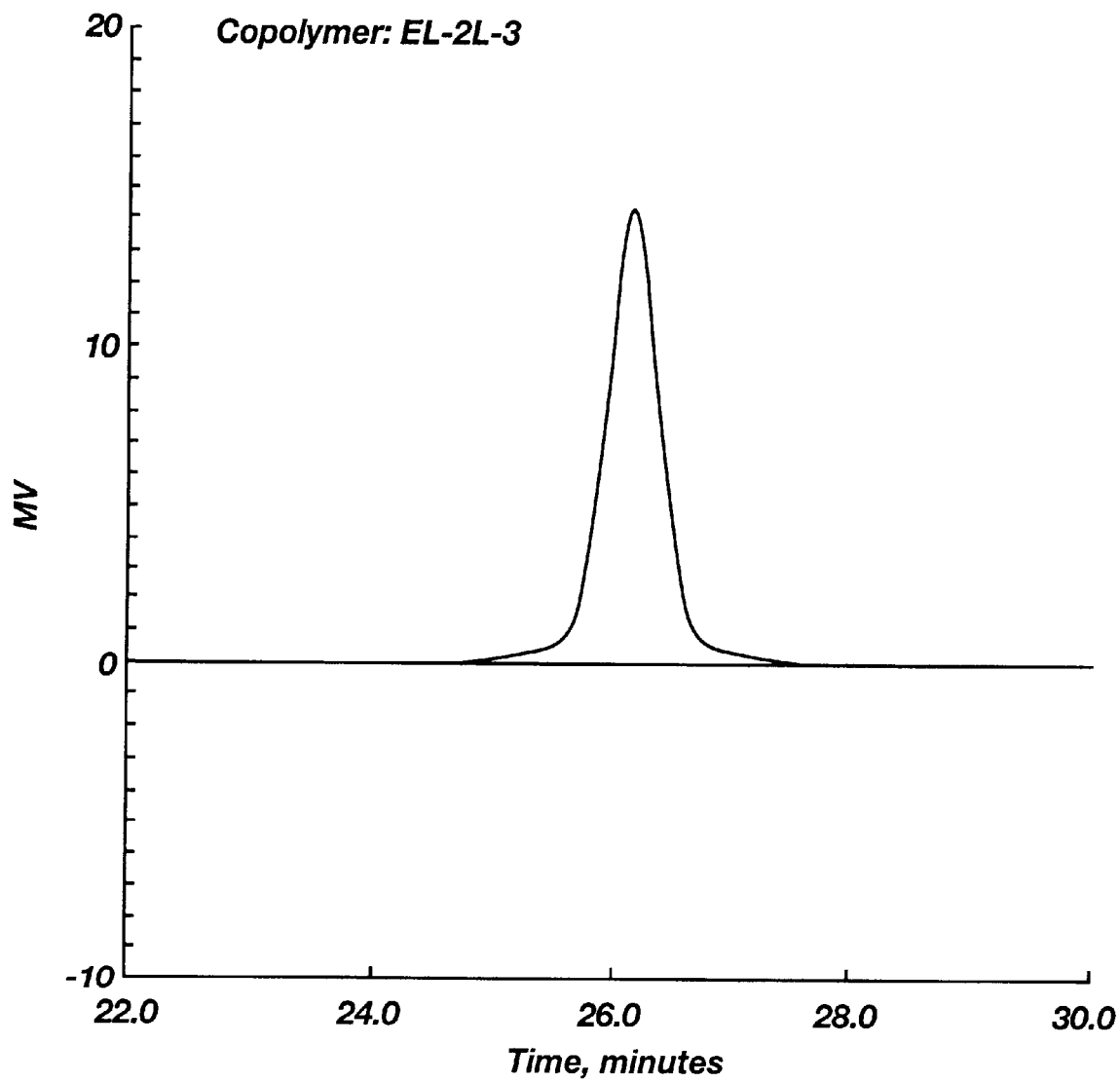
FIG. 1 is the GPC(gel permeation chromatography) trace of the monomethoxy poly(ethylene oxide)-poly(lactic acid) diblock copolymer(EL-2L-3)(column: MT3-MT4(Waters, U.S.A.), flow rate: 10 ml/min, eluent: tetrahydrofuran).

The biodegradable polymeric micelle-type drug composition of the present invention comprises a biodegradable polymeric micelle made of a biodegradable amphiphilic block copolymer and, having physically entrapped therein, one or more hydrophobic drugs, and, when administered, the hydrophobic biodegradable polymer decomposes by simple hydrolysis in vivo into non-toxic small molecules.

Biodegradable polymeric micelles having an average diameter of 10 to 100 nm are particularly suitable for formulating a soluble injection composition of hydrophobic drugs which are either insoluble or only slightly soluble in water.

The biodegradable polymeric micelle of the amphiphilic block copolymer of the present invention may be prepared by combining a biodegradable hydrophobic polymer, e.g., poly(lactic acid), poly(glycolic acid), poly(lactic-co-glycolic acid), poly(ε-caprolactone), and derivatives thereof with a hydrophilic polymer such as poly(alkylene oxide). A hydrophobic drug may be delivered to a warm blooded animal much more effectively when it is carried by the polymeric micelle of the present invention and sustained release of the drug incorporated in the micelle enhances the therapeutic effect of the drug.

The block copolymer used in the drug composition of the present invention may be a polymer of formula (I), (II) or (III):

$$R_1\text{—}(\text{—OCH}_2\text{CH}_2\text{—})_m\text{—X} \quad (I)$$

$$X\text{—}(\text{—OCH}_2\text{CH}_2\text{—})_m\text{—X} \quad (II)$$

$$R_1\text{—}(\text{—OCH}_2\text{CH}_2\text{—})_m\text{—X—}(\text{CH}_2\text{CH}_2\text{O—})_m\text{—R}_1 \quad (III)$$

wherein, $R_1$ is hydrogen or $C_{1-20}$ alkyl, preferably $C_{1-5}$ alkyl; m is an integer larger than 2, preferably from 20 to 75; and X is a biodegradable hydrophobic polymer segment having a molecular weight more than 100, preferably 300–4,000, and it is preferably selected from the group consisting of poly (lactic acid), poly(glycolic acid), poly(lactic-co-glycolic acid), poly(ε-caprolactone) and derivatives thereof. Preferably, the amphiphilic block copolymer has a molecular weight in a range of about 1430 to about 6000 Daltons and the hydrophilic component content is in a range of about 50 wt % to about 70 wt % based on the total weight of the block copolymer.

As described above, while poly(ethylene oxide) may be used as the preferred hydrophilic component of the block copolymer of the present invention, the hydrophobic component of the block copolymer of the present invention may comprise poly(lactic acid), poly(glycolic acid), poly(lactic-co-glycolic acid), poly(e-caprolactone), derivatives thereof and the like having the following structures:

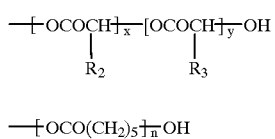 (IV)

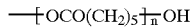 (V)

 (V)

wherein $R_2$ and $R_3$ are independently H or $CH_3$; x, y and n are independently integers larger than 2, preferably from 2 to 45.

The more preferable block copolymer which may be used in the drug composition of the present invention are di- or tri-block copolymers of formulas (VI), (VII), (VIII) and (IX):

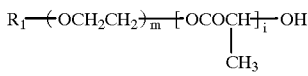 (VI)

 (VII)

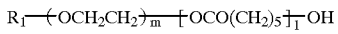 (VIII)

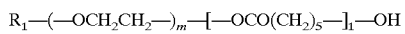 (VIII)

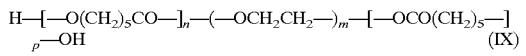 (IX)

wherein $R_1$ is hydrogen or $C_{1-20}$ alkyl, preferably it is $C_{1-5}$ alkyl; i is an integer larger than 2, preferably from 2 to 55; j and k are independent integers larger than 1, preferably from 2 to 55; l is an integer larger than 2, preferably from 2 to 35; m is as described above; and n and p are independent integers larger than 1, preferably from 2 to 35.

Diblock and triblock copolymers(BA type and ABA type) may be composed of a poly(ethylene oxide)(PEO) hydrophilic component(B) and a poly(lactic acid) hydrophobic component(A), as shown in formulae (X) and (XI):

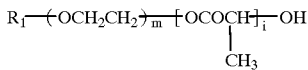 (X)

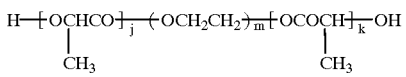 (XI)

wherein i, j, k and m are as described above.

BA type di-block or ABA type tri-block copolymers of the present invention may be prepared by ring-opening polymerization. For example, the BA type diblock copolymer composed of PEO as the hydrophilic component(B) and PLA as the hydrophobic component(A) may be prepared by using PEO having a methoxy group at one terminal and a hydroxy group at the other terminal. The ABA type triblock copolymer may be prepared by using PEO having hydroxy groups at both terminals. The ability of the block copolymer to solubilize the hydrophobic drug in water may be regulated by controlling the ratio of the hydrophilic component and hydrophobic component.

Another embodiment of the biodegradable polymeric micelle of the amphiphilic block copolymer of the present invention is a BAB type tri-block copolymer which may be represented by Formula XII:

(XII)

Wherein R is an alkyl group such as $CH_3(CH_2)_p$ where p=0~6;and X is —C(=O)(CH$_2$)$_q$C(=O)— or —C(=O)NH(CH$_2$)$_q$NHC(=O) —or —C(=O)—C$_6$H$_4$—C(=O)— where q=1~10.

It is important that the average molecular weight of the BAB type tri-block copolymer be less than 6,000 Daltons, and the content of the combined poly (ethylene oxide) (PEO) ranges from 50 to 70% by weight of the block copolymer. Preferably, each PEO block has a molecular weight ranging from 200 to 2,100 Daltons, and the each hydrophobic PLA block has a molecular weight ranging from 200 to 3,000 Daltons.

While mPEO-PLA(B-A) or PLA-PEO-PLA(A-B-A) type di- or tri-block copolymers can be synthesized by direct ring opening polymerization of lactide in the presence of both a metal catalyst (Stannous Octoate) and poly (ethylene oxide), the PEO-PLA-PEO (B-A-B) type tri-block copolymer cannot be synthesized by the direct ring opening polymerization. However, a PEO-PLA-PEO (B-A-B) type tri-block copolymer can be synthesized by a coupling reaction of mPEO-PLA-OH (B-A) di-block copolymer with appropriate coupling agents as in the following two methods.

The B-A-B type tri-block copolymers may be synthesized by using the di-block copolymers and in accordance with the coupling reactions (1):

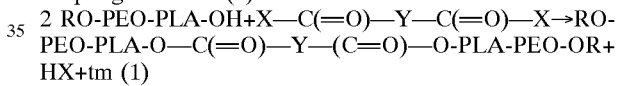

wherein R is an alkyl group such as $CH_3(CH_2)_s$, where s=0~6; and X is HO, Cl, or Br; and Y is —(CH$_2$)$_t$— or —C$_6$H$_4$—where t is an integer of 1 to 10.

The coupling agents that can be used in the above coupling reactions have two reactive groups in the molecule, and preferably are biocompatible compounds which can be metabolized in vivo, for example, an organic di-acid selected from oxalic acid, malonic acid, succinic acid, glutaric acid, adipic acid, phthalic acid, and acid chlorides and bromides thereof. In the case of using an organic di-acid, it is desirable to employ a suitable dehydrating agent such as dicyclo carbodiimide, oxalic acid chloride, thionyl chloride or triphenyl phosphine.

Alternatively, the B-A-B type tri-block copolymers may be synthesized by using a diisocyanide derivative in accordance with the urethane coupling reaction (2):

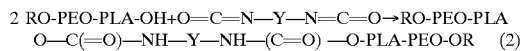 (2)

Wherein R is an alkyl group such as $CH_3(CH_2)_s$ where s=0~6; and Y is —(CH$_2$)$_t$— or —C$_6$H$_4$—, where t is an integer of 1~10.

Suitable hydrophobic drugs which may be incorporated into the block copolymer drug_carrier micelle of the present invention can be any bioactive agent having limited solubility in an aqueous or hydrophilic environment. Without limiting the scope of the present invention, suitable hydrophobic agents include anti-cancer drugs, antiphlogistic anodynes, immuno-suppressants, hepatism remedies, hormone compositions, chemotherapeutics, metabolic pharmaceuticals, digestive disease remedies, respiratory disease remedies, anti-allergic pharmaceuticals, central nervous system disease remedies, peripheral disease remedies, and circulatory disease remedies. The preferred hydrophobic drugs suitable for use in the present invention is a member selected from the group consisting of: paclitaxel, doxorubicin, teniposide, etoposide, daunomycin, methotrexate, mitomycin C, indomethacin, ibuprofen, cyclosporine, and biphenyl dimethyl dicarboxylate(DDB). The most preferred hydrophobic drug suitable for the present invention is a member selected from the group consisting of paclitaxel, doxorubicin, and cyclosporine.

In order to incorporate or solubilize one or more drugs mentioned above into the block copolymer micelle, various methods described below may be used alone or in combination.

(1) Stirring

A drug is added to an aqueous solution of a block copolymer, and stirred for 2 to 24 hours to obtain micelles containing the physically entrapped drug.

(2) Heating

A drug and a block copolymer are dissolved in an organic solvent and the solvent is evaporated off at an elevated temperature (40~80° C. under a nitrogen atmosphere or by rotary evaporator under vacuum). The resulting mixture is kept at a temperature of 20~80° C., preferably at 40~70° C., for 2 hours. Then, warm water (40~70° C.) is added thereto, and the mixture is stirred until a polymeric micelle containing drug is formed.

(3) Ultrasonic Treatment

A mixture of a drug and an aqueous solution of a block copolymer is subjected to ultrasonic treatment for a period ranging from about 1 second to 1 hour and then stirred at room temperature to obtain micelles containing the drug.

(4) Solvent Evaporation

A drug is dissolved in a water-immiscible organic solvent, for example, dichloromethane, chloroform and the like, and then added to an aqueous solution of a block copolymer. Subsequently, the organic solvent is slowly evaporated off at 25–40° C. while stirring, and then filtered to remove undissolved drug.

(5) Dialysis

A drug and a block copolymer are dissolved in a water-miscible organic solvent. The solution is dialyzed against a buffer solution and then against water.

In the dialysis method, suitable water-miscible organic solvents for dissolving drugs are selected from the group consisting of acetonitrile, dimethylformamide(DMF), dimethylsulfoxide(DMSO), dioxane, dimethylacetamide (DMAC) and the like.

Figure 2:
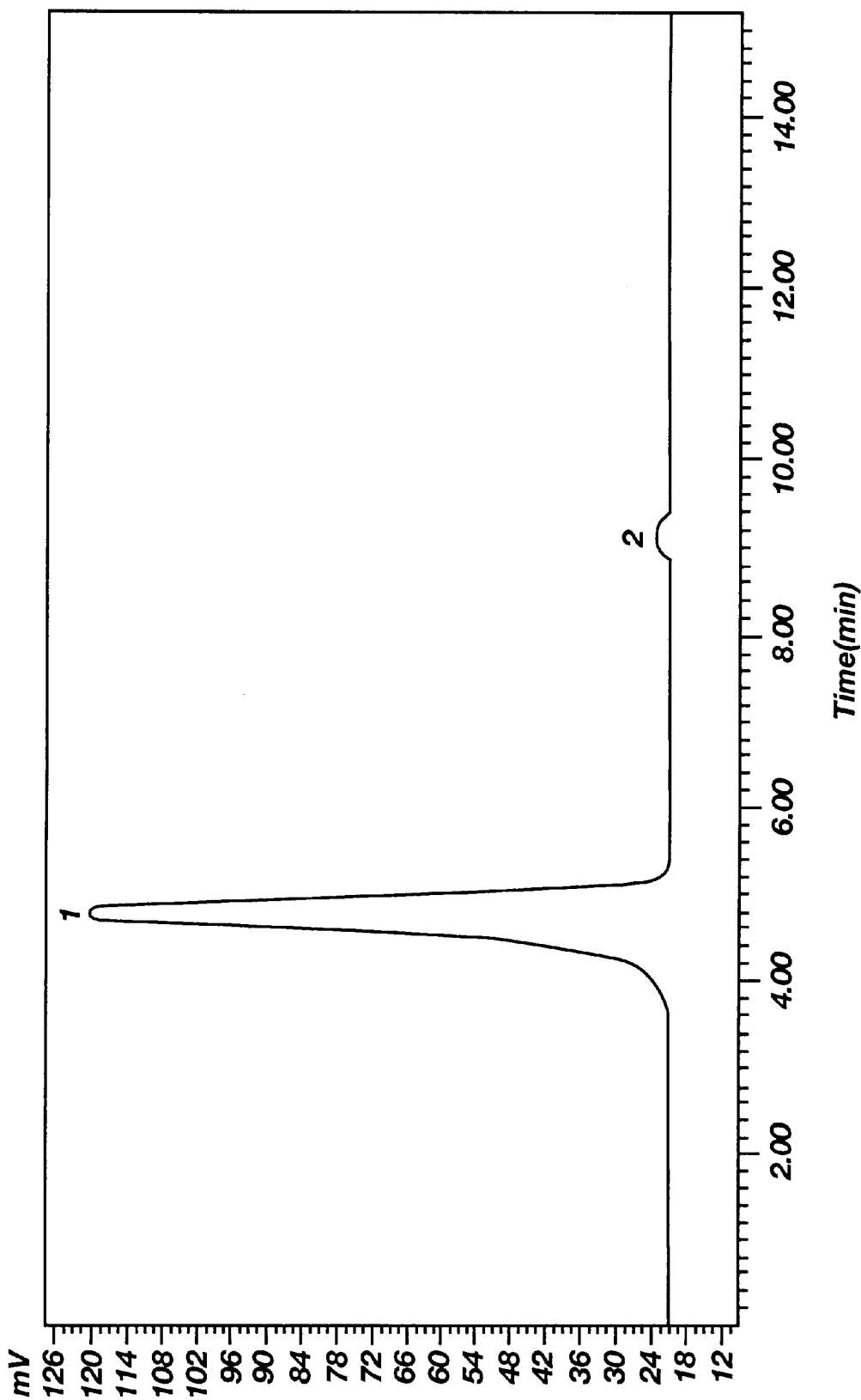
FIG. 2 is the GPC(gel permeation chromatography) trace of the monomethoxy poly(ethylene oxide)-polycaprolactone diblock copolymer(EC-2C-1 )(column: Asahipak GS 520H, eluent: distilled water).

The amphiphilic block copolymers of the present invention form stable micelles having an average size of 10–60 nm as shown in Table 1 and 4 of the Examples. Micelles of this size range are suitable for injection formulations. The stability of the micelles is excellent, as can be seen from the gel permeation chromatography shown in FIG. 2. Furthermore, a hydrophobic drug may be incorporated into the biodegradable polymeric micelle of the present invention by methods other than those described above, wherein the amount and physical state of the incorporated drug may vary depending on the composition of the block copolymer and also on the method of preparing the polymer micelle(Tables 1, 2 and 3). Since the drug held in the compact core of the hydrophobic component is released in vitro in a controlled manner(FIG. 3), the composition of the present invention is particularly suitable for drugs which are not amenable to conventional formulating techniques.

For example, paclitaxel is an outstanding anti-cancer agent but formulation thereof is difficult, mainly due to its low water-solubility. For this reason, a paclitaxel formulation containing Cremophor EL as the adjuvant is currently on the market, although Cremophor EL may cause some serious side effects, e.g., allergic reactions. This particular formulation has other problems: i.e., it tends to form minute precipitates which require the use of a filter in the injection line; and the required period of administration is long, about 24 hours.

Figure 3:
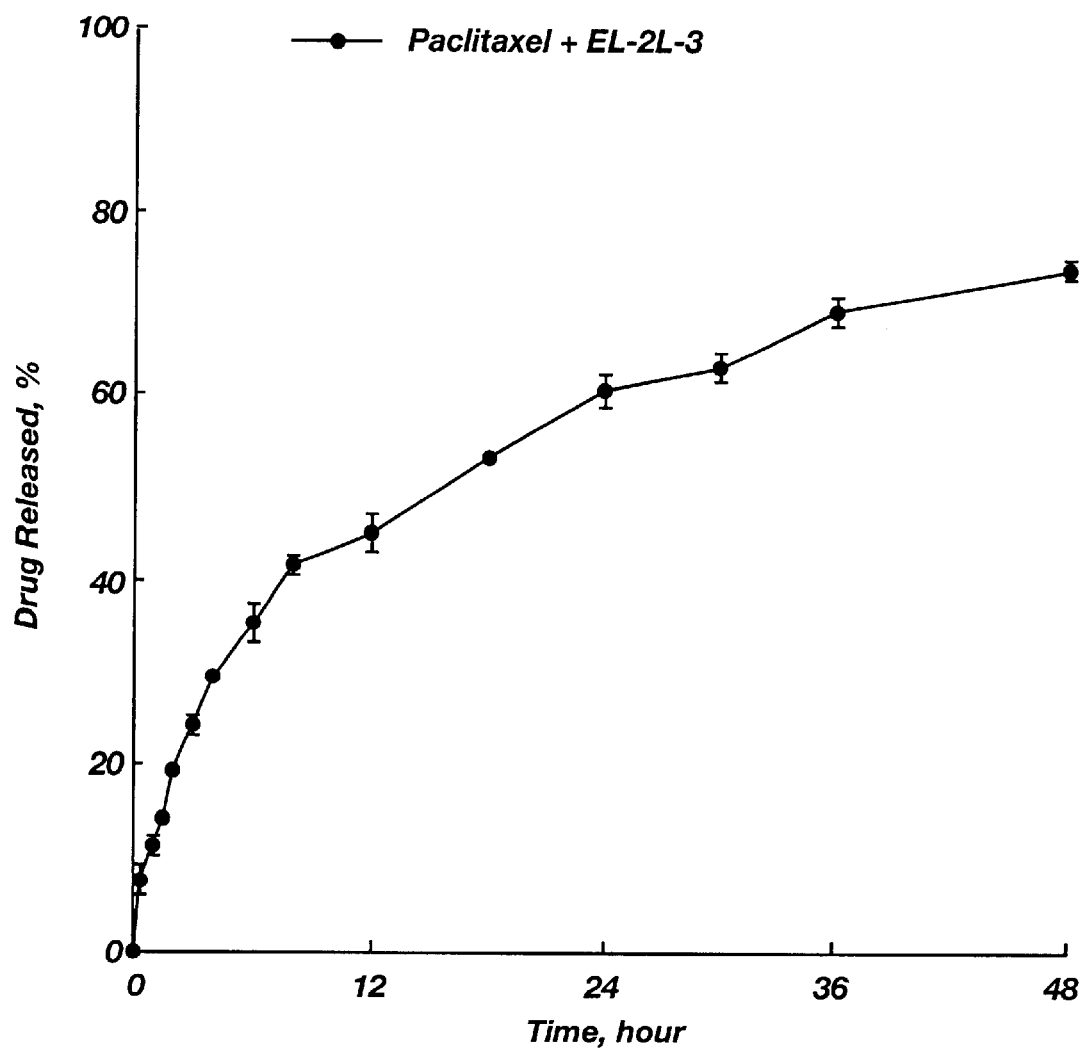
FIG. 3 shows the release profiles of paclitaxel incorporated in the EL-2L-3 copolymer micelle.
Figure 4:
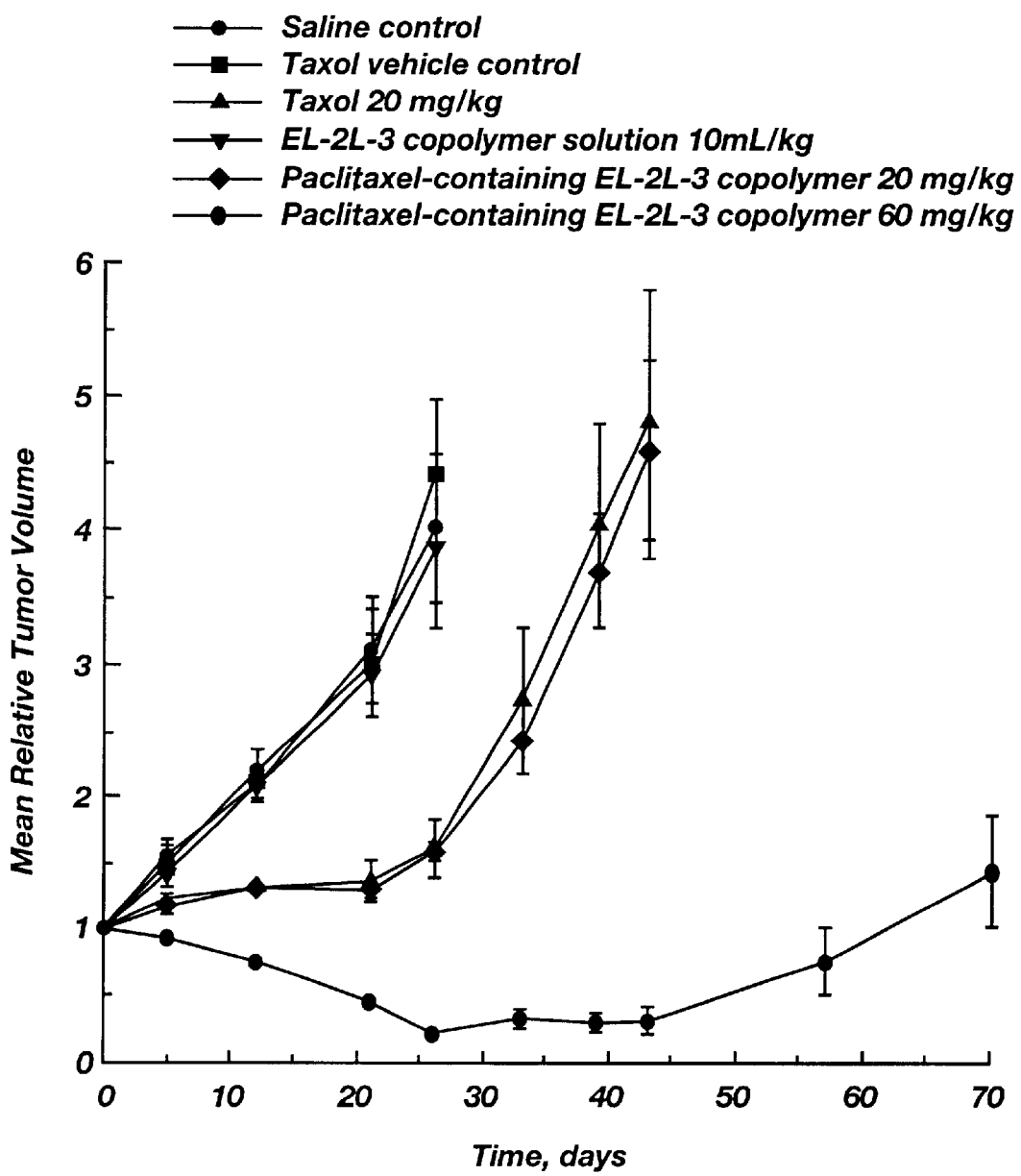
FIG. 4 shows the anticancer activity of paclitaxel incorporated in the EL-2L-3 copolymer micelle.

In contrast, the biodegradable polymeric micelle of the present invention greatly enhances the solubility of paclitaxel, and the biodegradable polymeric micelle-paclitaxel composition thus obtained is essentially non-toxic and exhibits enhanced anti-cancer therapeutic activity (FIG. 4, Table 5 and 6). In addition, the amounts of paclitaxel and cyclosporin A incorporated into the particular biodegradable polymeric micelles can reach up to 23.4±2.40% and 23.1±2.31% respectively (Tables 2 and 3). Furthermore, the biodegradable polymeric micelle-paclitaxel composition of the present invention released 70% of the incorporated paclitaxel continuously over a period of 48 hours, while effectively preventing the cancer cells from growing (FIG. 3). In view of the above referenced results, the biodegradable polymeric micelle-paclitaxel composition of the present invention is superior to conventional formulations in terms of toxicity, adverse effects and effectiveness.

The amount of incorporated drug is highest when an amphiphilic di/tri block copolymer having a molecular weight of about 1430 to about 6000 Daltons is used, wherein the hydrophilic component is poly(ethylene oxide) present in an amount of about 50 to about 70 wt % based on the total weight of the block copolymer; the hydrophobic component is poly(lactic acid) having a molecular weight of 4,000 or less. In this condition, the block copolymer composition containing paclitaxel can form a solution without forming precipitates when it is dispersed in water. Furthermore, a use of the polymeric micelle composition containing paclitaxel makes it possible to release the drug in a controlled-release manner.

The biodegradable polymeric micelle, prepared in accordance with the present invention, using an amphiphilic block copolymer is composed of a tightly packed hydrophobic polymer core and an outer hydrophilic polymer layer, the hydrophobic core being capable of taking up a significant amount of hydrophobic drug. The inventive biodegradable polymeric micelle has an higher aggregation number than conventional surfactant micelles above the critical micelle concentration (CMC) even when the higher molecular weight of the water soluble fraction of the amphiphilic block copolymer is used, and it is highly stable because the inner hydrophobic core is closely associated. In contrast, a low molecular weight surfactant has a lower aggregation number above the CMC, and lower stability because the inner hydrophobic component is more loosely associated. Such stabilized micelles are effective as drug carriers, and indeed, the inventive micelle readily takes up a hydrophobic drug into its hydrophobic core to produce a solution of the drug. Thus, the inventive micelle acts as a solubilizing agent for a hydrophobic drug. The drug solution thus obtained may be freeze-dried for long-term storage, and the lyophilized biodegradable polymeric micelle-type drug composition may be restored to its original solution by using water or an isotonic solution.

The only limitation as to how much drug can be loaded into the biodegradable and water soluble micelle of the present invention is one of functionality, namely, the drug/ micelle copolymer load may be increased until the micelle structure, and/or the properties of the copolymer, are adversely affected to an unacceptable degree, or until the properties of the system are adversely affected to such a degree as to make administration of the system unacceptably difficult. Certain newly synthesized or genetically engineered drugs are active at very minute concentrations. Generally speaking, it is anticipated that in most instances the drug/copolymer will make up between about $10^{-6}$ to about 30 percent by weight of the micelle copolymer with ranges of between about 0.001 to 25% being most common. These ranges of drug/micelle copolymer loading are illustrative and will include most hydrophobic drugs that may be utilized in the present invention. However, such ranges are not limiting to the invention should drug loadings outside this range be functional and effective.

According to this invention, the concentration of drug-copolymer micelles that can be dissolved in an aqueous solution is preferably within the range of about 0.001 to 40% by weight. However, such ranges are not limiting to the invention should concentrations outside this range be functional and effective. The hydrophobic drug carrying micelle composition of the present invention may be administered orally, parenterally, topically, transdermally, transmucosally, or transurethrally.

The present invention thus provides a biodegradable polymeric micelle-type drug composition which is physically more stable, therapeutically more effective, and toxicologically much safer than conventional formulations of hydrophobic drugs. The following Preparation Examples and Examples are provided for the purpose of illustrating certain aspects of the present invention only; they are not to be construed as limiting the scope of the present invention in any way. In these examples the terms PEG and PEO are used interchangeably.

PREPARATION EXAMPLE 1

Synthesis of Polylactide-Poly(ethylene oxide)-Polylactide (ABA) Triblock Copolymer (EL-3L-0)

2.00 g of poly(ethylene glycol)(Mw 2000) was dried under a reduced pressure at 120° C. for 2 hours and 1.0 mg of stannous octoate in toluene(amount corresponding to 0.1% of D,L-lactide) was added thereto as a catalyst. The resulting mixture was subjected to a reduced pressure at 100° C. for 20 to 30 minutes to remove volatile compounds, mixed with 1.00 g of D,L-lactide, and the mixture was reacted at 130° C. for 13 hours.

The block copolymer thus obtained was dissolved in 10 ml of chloroform and then an excess amount of diethyl ether was added, with stirring, to induce precipitation of the polymer. The precipitate was filtered and washed several times with diethyl ether, and then dried under a reduced pressure at 30° C. for one day to obtain 2.79 g of a tri-block copolymer, polylactide-poly(ethylene oxide)-polylactide (PLA-PEO-PLA), designated EL-3L-0(yield 93%). The properties of this block copolymer are listed in Table 1.

PREPARATION EXAMPLE 2

Synthesis of Polylactide-Poly(ethylene oxide)-Polylactide (ABA) Triblock Copolymer (EL-3L-1).

The procedure of Preparation Example 1 was repeated, except for using 2.00 g of poly(ethylene glycol)(Mw 2000) and 1.20 g of D,L-lactide, to obtain 2.91 g of a triblock copolymer, polylactide-poly(ethylene oxide)-polylactide (PLA-PEO-PLA), designated EL-3L-1(yield 91%). The properties of this block copolymer are listed in Table 1.

PREPARATION EXAMPLE 3

Synthesis of Polylactide-Poly(ethylene oxide)-Polylactide (ABA) Tri-block Copolymer (EL-3L-2)

The procedure of Preparation Example 1 was repeated, except for using 2.00 g of poly(ethylene glycol)(Mw 2000) and 1.60 g of D,L-lactide, to obtain 3.35 g of a tri-block copolymer, polylactide-poly(ethylene oxide)-polylactide (PLA-PEO-PLA), designated EL-3L-2(yield 93%). The properties of this block copolymer are listed in Table 1.

PREPARATION EXAMPLE 4

Synthesis of Polylactide-Poly(ethylene oxide)-Polylactide (ABA) Triblock Copolymer (EL-3L-3)

The procedure of Preparation Example 1 was repeated, except for using 2.00 g of poly(ethylene glycol)(Mw 2000) and 2.00 g of D,L-lactide, to obtain 3.56 g of a triblock copolymer of polylactide-poly(ethylene oxide)-polylactide (PLA-PEO-PLA), designated EL-3L-3(yield 89%). The properties of this block copolymer are listed in Table 1.

PREPARATION EXAMPLE 5

Synthesis of Poly(ethylene oxide)-Polylactide (BA) Diblock Copolymer (EL-2L-0)

The procedure of Preparation Example 1 was repeated, except for using 2.00 g of monomethoxy poly(ethylene glycol)(Mw 2000) and 0.50 g of D,L-lactide, to obtain 2.30 g of a diblock copolymer of monomethoxy poly(ethylene oxide)-polylactide(mPEO-PLA), designated EL-2L-0(yield 92%). The properties of this block copolymer are listed in Table 1.

PREPARATION EXAMPLE 6

Synthesis of Poly(ethylene oxide)-Polylactide (BA) Diblock Copolymer (EL-2L-1)

The procedure of Preparation Example 1 was repeated, except for using 2.00 g of monomethoxy poly(ethylene glycol)(Mw 2000) and 1.00 g of D,L-lactide, to obtain 2.70 g of a diblock copolymer of monomethoxy poly(ethylene oxide)-polylactide(mPEO-PLA), designated EL-2L-1(yield 90%). The properties of this block copolymer are listed in Table 5 1.

PREPARATION EXAMPLE 7

Synthesis of Poly(ethylene oxide)-Polylactide (BA) Diblock Copolymer (EL-2L-2)

The procedure of Preparation Example 1 was repeated, except for using 2.00 g of monomethoxy poly(ethylene glycol)(Mw 2000) and 1.50 g of D,L-lactide, to obtain 3.15 g of a diblock copolymer of monomethoxy poly(ethylene oxide)-polylactide(mPEO-PLA), designated EL-2L-2(yield 90%). The properties of this block copolymer are listed in Table 1.

PREPARATION EXAMPLE 8

Synthesis of Poly(ethylene oxide)-Polylactide (BA) Diblock Copolymer (EL-2L-3)

The procedure of Preparation Example 1 was repeated, except for using 2.00 g of monomethoxy poly(ethylene glycol)(Mw 2000) and 1.80 g of D,L-lactide, to obtain 3.46 g of a diblock copolymer of monomethoxy poly(ethylene oxide)-polylactide(mPEO-PLA), designated EL-2L-3 (yield 91%). The properties of this block copolymer are listed in Table 1 and the result of gel permeation chromatography are shown in FIG. 1.

PREPARATION EXAMPLE 9

Synthesis of Polycaprolactone-Poly(ethylene oxide)-Polycaprolactone (ABA) Triblock Copolymer(EC-3C-1)

The procedure of Preparation Example 1 was repeated, except for using 2.00 g of poly(ethylene glycol)(Mw 2000) and 1.60 g of caprolactone, to obtain 3.24 g of a triblock copolymer of polycaprolactone-poly(ethylene oxide)-polycaprolactone(PCL-PEO-PCL), designated EC-3C-1 (yield 90%). The properties of this block copolymer are listed in Table 1.

PREPARATION EXAMPLE 10

Synthesis of Poly(ethylene oxide)-Polycaprolactone (BA) Diblock Copolymer (EC-2C-1)

The procedure of Preparation Example 1 was repeated, except for using 2.00 g of monomethoxy poly(ethylene glycol)(Mw 2000) and 1.50 g of caprolactone, to obtain 3.20 g of a diblock copolymer of monomethoxy poly(ethylene oxide)-polycaprolactone(mPEO-PCL), designated EC-2C-1 (yield 91%). The properties of this obtained block copolymer are listed in Table 1.

PREPARATION EXAMPLE 11

Synthesis of mPEO-PLA (BA) Diblock Copolymer 20.0 g (10 mmole) of monomethoxy poly(ethylene glycol) (Mw 2,000) in a 2-necked 100 ml round-bottomed flask was dried under a reduced pressure (1 mmHg) at 100° C. for 3 hours and dry nitrogen was introduced therein. 76 mg of stannous octoate in toluene, in an amount corresponding to 0.5 mol % of lactide was added thereto using a syringe. The resulting mixture was stirred for 30 minutes at 110° C. under a reduced pressure (1 mmHg) to remove toluene. 5.4 g of D,L-Lactide was added thereto and the mixture was allowed to react at 110° C. for 24 hours.

The polymer obtained was dissolved in dichloromethane, and then, diethyl ether was added thereto with stirring to induce precipitation of the polymer. The precipitated polymer was dried in vacuum oven for 48 hours to obtain an mPEO-PLA diblock copolymer (Mw mPEO2,000-PLA900). The mPEO content of this copolymer was 69 wt %.

PREPARATION EXAMPLE 12

Synthesis of mPEO-PLA (BA) Diblock Copolymer

The procedure of Example 11 was repeated using 20.0 g of monomethoxy poly (ethylene glycol) (Mw 1,000), 22.8 g of D,L-lactide and 128.3 mg of stannous octate to obtain an mPEO-PLA diblock copolymer(Mw PEO1,000-PLA950). The mPEO content of this copolymer was 51 wt %.

PREPARATION EXAMPLE 13

Synthesis of mPEO-PLA-mPEO (BAB) Triblock Copolymer (EL-3L-4)

11.2 g(3.86 mmole) of the mPEO-PLA-OH(Mw 2,000-900) diblock copolymer synthesized in Example 11 and 0.30 g (2 mmole) of succinyl dichloride were added to 50 ml of toluene, 1 ml of pyridine was added thereto, and the mixture was stirred at 120° C. for 12 hours. Toluene was removed by evaporating and the resulting product was dissolved in dichloromethane, followed by removing solids by filtration. The filtrant was added to diethyl ether, and the precipitated polymer was filtered and dried in vacuum for 24 hours to obtain 9.85 g of an mPEO-PLA-mPEO (Mw PEO2,000-PLA1,800-PEO2,000) BAB triblock copolymer (yield 88%).

PREPARATION EXAMPLE 14

Synthesis of mPEO-PLA-mPEO (BAB) Triblock Copolymer(EL-3L-5)

The procedure of Example 13 was repeated using 10.0 g (5.13 mmole) of the mPEO-PLA-OH (Mw 1,000-950) di-block copolymer synthesized in Example 12 and 0.35 g (2.6 mmole) of 1,6-diisocyanohexane, to obtain mPEO-PLA-mPEO (Mw PEO1,000-PLA1,900-PEO1,000) triblock copolymer (yield 89%).

PREPARATION EXAMPLE 15

Preparation of Polymeric Micelle

Each of the block copolymers synthesized in Preparation Examples 1–10, 13 and 14 was dissolved in distilled water or 0.1 M phosphate buffer(pH 7.4) to a concentration of 0.01 to 5% (w/v) to obtain a polymeric micelle solution. The size of the micelle in each polymeric micelle solution of Examples 1 through 9, measured by dynamic light scattering method, was in the range from 10 to 60 nm as shown in Table 1. Polymeric micelles of this size are suitable for use as drug carriers. The formation of the polymeric micelle made of the copolymer of EC-2C-1 prepared in Preparation Example 10 was confirmed by the gel permeation chromatography in FIG. 2.

TABLE 1

| Copolymer | Calculated Composition | Measured Composition[a] | Yield (%) | Solubility (g/100 ml) | Size [b] (nm) |
| --- | --- | --- | --- | --- | --- |
| EL-3L-0 | PLA500-PEO2000-PLA500 | PLA470-PEO2600-PLA470 | 93 | over 20 | 13 ± 3.2 |
| EL-3L-1 | PLA600-PEO 2000-PLA600 | PLA550-PEO 2000-PLA550 | 91 | over 20 | 26 ± 2.5 |
| EL-3L-2 | PLA800-PEO 2000-PLA800 | PLA735-PEO 2000-PLA735 | 93 | 10 | 45 ± 4.1 |
| EL-3L-3 | PLA1000-PEO 2000-PLA1000 | PLA930-PEO 2000-PLA930 | 89 | 3 | 48 ± 4.8 |
| EL-2L-0 | mPEO2000-PLA500 | mPEO2000-PLA460 | 92 | over 20 | 12 ± 1.2 |
| EL-2L-1 | mPEO2000-PLA1000 | mPEO2000-PLA915 | 90 | over 20 | 25 ± 2.4 |
| EL-2L-2 | mPEO2000-PLA1500 | mPEO2000-PLA1370 | 90 | over 20 | 35 ± 3.1 |
| EL-2L-3 | mPEO2000-PLA1800 | mPEO2000-PLA1675 | 91 | over 20 | 33 ± 3.5 |

TABLE 1-continued

| Copolymer | Calculated Composition | Measured Composition[a] | Yield (%) | Solubility (g/100 ml) | Size [b] (nm) |
|---|---|---|---|---|---|
| EC-3C-1 | PCL800-PEO 2000-PCL800 | PCL725-PEO 2141-PCL725 | 90 | 3 | 45 ± 3.6 |
| EC-2C-1 | mPEO2000-PCL1500 | mPEO2600-PCL1390 | 91 | 4 | 52 ± 2.9 |

[a]1H NMR (solvent: CDCl$_3$)
[b]dynamic light scattering

EXAMPLE 1

Preparation of Block Copolymer Micelles Containing Paclitaxel (1) Incorporation of paclitaxel into EL-3L-2, EL-2L-3 and EC-2C-1 by the stirring method 10 mg of each of the block copolymers EL-3L-2, EL-2L-3 and EC-2C-1 synthesized in Preparation Examples 3, 8 and 10 was dissolved in 3 ml of distilled water and 5 mg of paclitaxel, an anticancer drug which is hardly soluble in water, was added thereto and stirred for 2 hours. The resulting solution was filtered with a 0.45 μm membrane filter to remove undissolved paclitaxel and a clear solution of block copolymer micelles containing paclitaxel was obtained. The amount of paclitaxel incorporated into the polymeric micelle dispersed in 1 ml of water was determined by HPLC column: Curosil-PFP(4.6×250 mm, 5 μm particle size, Phenomenex, U.S.A., mobile phase: acetonitrile/distilled water=45:55% (v/v)). The results are shown in Table 2.

(2) Incorporation by Solvent Evaporation 10 mg of EL-3L-2 synthesized in Preparation Example 3 was dissolved in distilled water, and a chloroform solution containing 3 mg of paclitaxel was slowly added thereto. The resulting mixture was stirred at room temperature overnight while allowing chloroform to evaporate. The resulting solution was filtered with a 0.45 μm membrane filter to remove unsolubilized paclitaxel and a clear solution of block copolymer micelles containing paclitaxel was obtained. This procedure was repeated using EL-2L3 and EC-2C-1 synthesized in Preparation Example 8 and 10. The amount of paclitaxel incorporated into the polymeric micelle was determined by the same method as above. The results are shown in Table 2.

(3) Incorporation by Dialysis 5 mg of paclitaxel was dissolved in 5 ml of DMF. EL-3L-2 synthesized in Preparation Example 3 was added to the resulting solution and the mixture was stirred overnight. The mixture was dialyzed against a 0.1 M phosphate buffer(pH 7.4) for 5 hours using a dialysis membrane (MWCO: 12000), and then against distilled water for 5 hours. The dialyzed solution was filtered with a 0.45 μm membrane filter and a clear solution of block copolymer micelles containing paclitaxel was obtained. This procedure was repeated using EL-2L-3 and EC-2C-1 synthesized in Preparation Example 8 and 10. The amount of paclitaxel incorporated into the polymeric micelle was determined by the same method as above. The results are shown in Table 2.

These experiments show that paclitaxel can be readily incorporated into the inventive polymeric micelles in amounts of up to 25%.

TABLE 2

| | Paclitaxel Incorporation Ratio (%) | | |
|---|---|---|---|
| Copolymer | Stirring | Solvent Evaporation | Dialysis |
| BL-3L-2 | 4.6 ± 0.52 | 15.5 ± 1.83 | 10.9 ± 1.50 |
| EL-2L-3 | 8.2 ± 0.65 | 23.4 ± 2.4 | 15.8 ± 1.83 |
| EC-2C-1 | 2.5 ± 0.24 | 17.5 ± 3.13 | 13.1 ± 1.45 |

Cf: Paclitexel Incorporated (%) = wt of Paclitaxel/(wt of copolymer + wt of Paclitaxel) × 100

EXAMPLE 2

Preparation of Block Copolymer Micelle Containing Cyclosporin A (1) Incorporation by Solvent Evaporation 10 mg of cyclosporin A, an immunosuppressant which is hardly-soluble in water, was dissolved in 1 ml of N,N-dimethyl acetamide and added slowly to a solution containing 20 mg of EL-2L-3 in 20 ml of distilled water. The resulting mixture was stirred overnight at room temperature while allowing N,N-dimethyl acetamide to evaporate off and the resulting solution was filtered with a 0.45 μm membrane filter to obtain a clear solution of the block copolymer micelles containing cyclosporin A. This procedure was repeated using EC-2C-1 synthesized in Preparation Example 10. The amount of cyclosporin A incorporated into the polymeric micelle was determined by the same method as in Example 1. The results are shown in Table 3.

(2) Incorporation by Dialysis 10 mg of cyclosporin A was dissolved in 5 ml of DMF. 20 mg of EL-2L-3 synthesized in Preparation Example 8 was added to the resulting solution and the mixture was stirred overnight. The mixture was dialyzed against 0.1 M phosphate buffer(pH 7.4) for 5 hours using dialysis membrane (MWCO: 12000), and then against distilled water for 5 hours. The dialyzed solution was filtered with a 0.45 μm membrane filter and a clear solution of block copolymer micelles containing cyclosporin A was obtained. This procedure was repeated using EC-2C-1 synthesized in Preparation Example 10. The amount of cyclosporin A incorporated into the polymeric micelle was determined by the same method described above. The results are shown in Table 3.

These experiments show that cyclosporin A can be readily incorporated in the inventive polymeric micelles in amounts of up to 25%.

TABLE 3

| | Cyclosporin Incorporation Ratio (%) | |
|---|---|---|
| Copolymer | Solvent Evaporation | Dialysis |
| EL-2L-3 | 21.5 ± 2.01 | 17.4 ± 1.55 |
| EC-2C-1 | 23.1 ± 2.31 | 17.0 ± 1.84 |

TABLE 3-continued

| | Cyclosporin Incorporation Ratio (%) | |
|---|---|---|
| Copolymer | Solvent Evaporation | Dialysis |

Cf: Cyclosporin Incorporated (%) = wt of Cyclosporin/(wt of copolymer + wt of Cyclosporin) × 100

EXAMPLE 3 mPEO-PLA-mPEO (Mw PEO2,000-PLA1,800-PEO2,000) Triblock Copolymer Micelle with Paclitaxel 5 mg of paclitaxel was dissolved in 0.5 ml of methylene chloride, and added slowly to a 3 ml aqueous solution containing 100 mg of mPEO-PLA-mPEGO tri-block copolymer synthesized in Example 12. The resulting aqueous solution was stirred at room temperature to evaporate methylene chloride and the resulting aqueous solution was filtered with a 0.45 μm membrane filter. This procedure was repeated using mPEO-PLA-m-PEO tri-block copolymer synthesized in Example 13. The results are summarized in Table 4.

TABLE 4

| | Copolymer | Micelle Size (nm) | Paclitaxel content (wt %) | Drug Loading efficiency (%) |
|---|---|---|---|---|
| EL-3L-4 | mPEO-PLA-mPEO (2,000-1,800-2,000) | 55 | 4.7 | 95 |
| EL-3L-5 | mPEO-PLA-mPEO (1,000-1,900-1,000) | 35 | 10 | 99 |

Cf: Paclitaxel Incorporated (%) = wt of Paclitaxel/(wt of copolymer + wt of Paclitaxel) × 100
Drug Loading efficiency = (Paclitaxel amount incorporated in polymeric Micelle/Initial added amount of Paclitaxel) × 100

EXAMPLE 4

Release Test 5 ml of the paclitaxel-containing EL-2L-3 copolymer micelle solution was placed in a dialysis sack(MWCO: 12,000). The sack was put into 1 L of $H_2O$, and the amount of paclitaxel A released from the micelles was determined. As can be seen from FIG. 3, the incorporated drug shows a sustained release profile.

EXAMPLE 5

Toxicity Test

In conducting the following tests, formulations of paclitaxel were obtained and/or prepared and compared against each other and, in some instances, against their respective carrier vehicles not containing paclitaxel. These formulations are identified as follows: (1) Taxol® (Bristol Myer Squibb trademark for a formulation of paclitaxel in a Cremophor EL (polyethoxylated castor oil) carrier vehicle; (2) Taxol® Vehicle Control (Cremophor EL (polyethoxylated castor oil); (3) Paclitaxel-containing EL-2L-3 Copolymer Micelle Solution; (4) EL-2L-3 Copolymer Micelle Vehicle Control.

(1) Rat Acute Toxicity ($LD_{50}$)

Twelve groups of Sprague Dawley rats (male/female, 4–5 weeks, 110–160 g) were given i.v. injections through the tail vein of following formulations respectively: 1) commercially formulated paclitaxel (Taxol®, from Bristol-Myers Squibb) at doses of 5.9, 8.0, 10.9, 14.7, 20 mg/kg; and paclitaxel-containing EL-2L-3 copolymer micelle solution at doses of 78, 109, 153, 214, 300 mg/kg. The survival and variation in body weight was observed daily over 21 days in all groups. $LD_{50}$ (Median Lethal Dose) was calculated by the Weil method using Labcat Module Ver. 4.26. The results are summarized in Table 5. These result clearly show the reduced toxicity (roughly 25 fold in these tests) resulting from usage of the copolymeric micelles of the present invention as compared to a commercial paclitaxel formulation.

(2) Maximum Tolerated Dose (MTD)

Eleven groups of C3H/HeNcrj mice (female, 8 weeks, 20±3 g) were given i.v. injections daily through the tail vein for three consecutive days of following formulations respectively: 1) commercially formulated paclitaxel Taxol®) at doses of 16, 26, 30, 33 mg/kg; and 2) paclitaxel-containing EL-2L-3 copolymer micelle solution at doses of 23,40, 45, 50, 55, 74 mg/kg. Mice survival and variation in body weight were observed daily over 30 days in all groups.

Six groups of CD1 nude (nu/nu) athymic mice (female, 6–8 weeks, 22–34 g) were given daily i.v. injections through the tail vein on a 0, 4, 8 day schedule of either commercially formulated paclitaxel(Taxol®) at doses of 20 mg/kg or paclitaxel-containing EL-2L-3 copolymer micelle solution at doses of 20, 40, 60, 80, 120 mg/kg. Mice survival and variation in body weight were observed daily over 30 days in all groups.

Thirteen groups of Tac:Cr:(NCr)-nu athymic mice (female, 6–7 weeks, 19±1 g) received daily i.v. injections through the tail vein for three consecutive days of commercially formulated paclitaxel (Taxol®)at doses of 15, 20, 25, 30, 35 mg/kg and paclitaxel-containing EL-2L-3 copolymer micelle solution at doses of45, 50, 55,60,70, 80, 90 mg/kg. Mice survival and variation in body weight were observed daily over 30 days in all groups.

The MTD was defined as the allowance of a median body weight loss of approximately 10–15% of the control and causes neither death due to toxic effects nor remarkable changes in the general signs within 2 weeks after drug administration. As shown in Table 5, the MTD in each of the tests was 2.5 to 3 times greater for the compositions of the present invention as compared to a commercial paclitaxel formulation.

TABLE 5

(Unit: mg/kg)

| | MTD Mice, female | | | $LD_{50}$ Sprague Dawley rats | |
|---|---|---|---|---|---|
| Toxicity | C3H/ | Tac:Cr: (Ncr)-nu | CDI nude | Male | Female |
| Animal | HeNcrj | athymic | (nu/nu) | | |
| Paclitaxel-containing EL-2L-3 copolymer micelle solution | 50 | 60 | 60 | 205.4 | 221.6 |
| Taxol ® | 26 | 20 | 20 | 8.3 | 8.8 |

(3) in-vitro Cytotoxicity

For the in vitro cytotoxicity test, the human breast cancer cell line MCF7 and the human ovarian cancer cell line OVCAR-3 were used. The cytotoxic activity of each study compound was evaluated in both human tumor cell lines at five ten fold dilutions ranging from 0.0001 up to 1 μg /mL.

Following continuous drug exposure for 4 days cells were stained with propidium iodide, which was detected by a fluorescence reader. The intensity of the obtained fluorescence signal correlates with the number of cells. The assays included untreated and positive controls (5-FU and vindesine). The results of two independent experiments were expressed as treatment over control (T/C) values and $IC_{70}$ values of each line. The fluorescence assay was performed essentially according to the method of Dengler et al (Anti-Cancer Drugs 1995;6:522–532). Briefly, cells were harvested from exponential phase cultures growing in RPMI 1640 medium supplemented with 10% fetal calf serum, counted and plated in 96 well flat-bottomed microtiter plates (100 cell suspension, $1 \times 10^5$ and $5 \times 10^4$ cells/mL for MCF7 and OVCAR-3, respectively). After a 24 h recovery, to allow cells to resume exponential growth, 50 culture medium (6 control wells per plate) or culture medium containing drug was added to the wells. Each drug concentration was plated in triplicate. Following 4 days of continuous drug exposure, non viable cells were stained by addition of 25 μL of a propidium iodide solution in sterile water (50 mg/ml). Fluorescence ($FU_1$) was measured using a Millipore Cytofluor 2350 microplate reader (excitation 530 nm, emission 620 nm). Microplates were then kept at −18° C. for 24 h, resulting in a total cell kill. After thawing of the plates and a second fluorescence measurement ($FU_2$) the amount of viable cells was calculated by $FU_2-FU_1$.

Paclitaxel-containing EL-2L-3 copolymer micelle solution, Taxol®, and, as controls, EL-2L-3 Copolymer Vehicle and Taxol Vehicle were tested for cytotoxicity in two human tumor cell lines in vitro. The control vehicles showed no toxicity at all concentrations tested (0.0001–1/mL). At the lowest concentration tested (0.001/mL) paclitaxel-containing EL-2L-3 copolymer micelle solution and Taxol® showed already growth inhibitory effects on the tumor cell lines with T/C values of approximately 61% and 91% for paclitaxel-containing EL-2L-3 copolymer micelle solution and Taxol®. At the highest concentration (1 μg/mL), paclitaxel-containing EL-2L-3 copolymer micelle solution and Taxol® showed already growth inhibitory effects on the tumor cell lines with T/C values of approximately 19% and 20%. The $IC_{70}$ values of the compound for the individual tumor cell lines and the mean $IC_{70}$ values were quite similar. Thus, the cytotoxicity of the compounds hardly differed. The results are summarized in Table 6.

TABLE 6

| Tumor cell line | $IC_{70}$ (μg/mL) | | | |
| --- | --- | --- | --- | --- |
| | Paclitaxel-containing EL-2L-3 copolymer micelle solution | Taxol ® | EL-2L-3 copolymer vehicle | Taxol ® vehicle |
| MCF7 | 0.002 | 0.002 | >1.000 | >1.000 |
| OVCAR-3 | 0.002 | 0.004 | >1.000 | >1.000 |
| Mean $IC_{70}$ | 0.002 | 0.003 | >1.000 | >1.000 |

EXAMPLE 6

Efficacy Test (1) Route of Administration and Dose Levels

Nude (nu/nu) athymic mice, which have been used extensively to generate human tumor xenografts, received i.v. injections of Taxol®, paclitaxel-containing EL-2L-3 copolymer micelle solution and control solutions of saline, Taxol® Vehicle, and EL-2L-3 Copolymer Vehicle as indicated below. The volume of carrier vehicle or saline is shown in terms of ml/kg of body weight. The dosage of paclitaxel in terms of mg/kg of body weight was administered in the same volume of carrier as in the respective vehicle controls. The test articles were administered 3 times: day 0 (where day 0 is the day of randomization), day 4 and day 8. There were 6 groups with 10 mice per group as follows:

| | | |
| --- | --- | --- |
| Group 1 | Saline Control | 20 ml/kg i.v. |
| Group 2 | Taxol ® Vehicle | 20 ml/kg i.v. |
| Group 3 | Taxol ® | 20 mg/kg i.v. |
| Group 4 | EL-2L-3 Copolymer Vehicle | 10 ml/kg i.v. |
| Group 5 | Paclitaxel-containing EL-2L-3 copolymer micelle solution | 20 mg/kg i.v. |
| Group 6 | Paclitaxel-containing EL-2L-3 copolymer micelle solution | 60 mg/kg i.v. |

(2) Procedure

Cells were taken from storage in liquid nitrogen and established as an in vitro cell culture. After harvesting, cells were washed in sterile phosphate buffered saline (PBS), and the number of viable cells were determined. Cells were re-suspended in sterile PBS at an approximate concentration of $7 \times 10^7$ cells/ml. Nude (athymic) mice were injected subcutaneously in the right flank with 0.1 ml of cell suspension containing approximately $7 \times 10^6$ cells. One hundred mice were implanted with the SKOV3 cell line. The mice were examined routinely for the appearance of tumors. Mice were allocated to groups on day 48 after tumor implantation. Treatment was also initiated on this day. Tumors were measured up to once weekly throughout this experiment.

Allocation to treatment groups was performed based on the volume of the individual tumors. Tumor measurement was performed using calipers to measure the tumor in two dimensions, at the longest and widest points. The two measurements were taken at approximately 90° to each other. Tumor volume was calculated from the formula $(W^2 \times L)/2$, where W is the shortest and L is the longest measurement. Tumors were ranked in descending order, according to volume, and mice were allocated into treatment groups. Only mice bearing SKOV3 tumors within the volume range 45.4–267.2 $mm^3$ were allocated to treatment groups (day 48 after tumor cell implant). Thirty mice were excluded due to insufficient tumor development at this time, or poor tumor shape. No mice were excluded due to excess tumor size on the day of randomization. Treatment was initiated on the day of randomization, day 48 after tumor implant.

Dosage treatment for Groups 1, 2 and 3 (saline, Taxol® Vehicle and Taxol®) was administered in a volume of 20 ml/kg. Dosage treatment for Groups 4, 5 and 6 (EL-2L-3 Copolymer Vehicle and that Vehicle containing the stated paclitaxel dosages) was administered in a volume of 10 ml/kg. Mice received a single i.v. dose on days 0, 4 and 8 (where day 0 is the day of randomization).

Tumor size was measured up to once per week for the duration of the study, including the day treatment was initiated (day 0) and the day mice were terminated from the study. As shown in FIG. 4, the growth of tumors for the saline and carrier vehicle groups not containing paclitaxel (Groups 1, 2 and 4) was essentially the same. The tumor growth for the 20 mg/kg paclitaxel dosage(Groups 3 and 5) was inhibited by the commercial Taxol® and EL-2L-3 micelle carrier formulations almost identically. However, due to the lower toxicity of the compositions of the present invention, larger dosages of paclitaxel can be administered. As shown by the inhibition of tumor growth of Group 6, administered the EL-2L-3 micelle formulation at a paclitaxel dosage of 60 mg/kg, clearly superior results in tumor inhibition were obtained.

In conclusion, water-insoluble, hydrophobic drugs can be readily loaded into the biodegradable block copolymer micelles of the present invention having a hydrophilic component and a hydrophobic component by way of either stirring, heating, ultrasonic treatment, solvent evaporation, dialysis and the like. The polymeric micelle drug composition thus obtained has a greatly improved pharmaceutical efficacy because a higher amount of the drug may be transferred effectively to a patient's body due to significantly reduced toxicity.

We claim:

1. A hydrophobic drug solution composition comprising an aqueous solvent carrier containing an effective amount of polymeric micelles which micelles consist essentially of:
   (a) 70 to 99.999999 percent by weight of biodegradable polymeric drug carrier micelles consisting essentially of an amphiphilic block copolymer consisting of BA diblock, ABA triblock and BAB triblock copolymers wherein the B block polymer component is a hydrophilic poly(alkylene oxide) component, and wherein the A block polymer component is a biodegradable hydrophobic polymer component selected from the group consisting of poly(lactic acid), poly(glycolic acid), poly(lactic-co-glycolic acid), and poly($\epsilon$-caprolactone), wherein the amphiphilic block copolymer has a molecular weight in the range of 1430 to 6000 Daltons and the hydrophilic B block component content is in a range of 50 wt % to 70 wt % based on the total weight of the block copolymer wherein said micelles are composed of a tightly packed hydrophobic polymer core and an outer hydrophilic polymer layer, and
   (b) 0.000001 to 30 percent by weight of a hydrophobic drug that is physically entrapped within and not covalently bound to said hydrophobic polymer core of said polymeric drug carrier micelles.

2. The composition of claim 1, wherein said polymeric drug carrier micelle is a member selected from the group consisting of ABA and BAB triblock copolymers.

3. The composition of claim 2, wherein said polymeric drug carrier micelle is an ABA tri-block copolymer.

4. The composition of claim 1, wherein the B block component is monomethoxy poly(alkylene oxide).

5. The composition of claim 1, wherein said hydrophilic poly(alkylene oxide) component has an average molecular weight in the range of 1000 to 3300 daltons.

6. The composition of claim 1, wherein said A block polymer is polylactide.

7. The composition of claims 1, wherein the hydrophobic drug is selected from the group consisting of: anti-cancer drugs, antiphlogistic anodynes, immuno-suppressants, hepatism remedies, hormone compositions, chemotherapeutics, metabolic pharmaceuticals, digestive disease remedies, respiratory disease remedies, anti-allergic pharmaceuticals, central nervous system disease remedies, peripheral disease remedies, and circulatory disease remedies.

8. The composition of claim 7, wherein the hydrophobic drug is selected from the group consisting of paclitaxel, doxorubicin, teniposide, etoposide, daunomycin, methotrexate, mitomycin C, indomethacin, ibuprofen, cyclosporine, and biphenyl dimethyl dicarboxylate(DDB).

9. The composition of claim 8, wherein the hydrophobic drug is selected from the group consisting of paclitaxel, doxorubicin, cyclosporine.

10. The composition of claim 9, wherein the hydrophobic drug is paclitaxel.

11. The composition of claim 10, wherein said A block polymer is polylactide.

12. The composition of claims 5, wherein the hydrophobic drug is selected from the group consisting of: anti-cancer drugs, antiphlogistic anodynes, immuno-suppressants, hepatism remedies, hormone compositions, chemotherapeutics, metabolic pharmaceuticals, digestive disease remedies, respiratory disease remedies, anti-allergic pharmaceuticals, central nervous system disease remedies, peripheral disease remedies, and circulatory disease remedies.

13. The composition of claim 12, wherein the hydrophobic drug is selected from the group consisting of: paclitaxel, doxorubicin, teniposide, etoposide, daunomycin, methotrexate, mitomycin C, indomethacin, ibuprofen, cyclosporine, and biphenyl dimethyl dicarboxylate(DDB).

14. The composition of claim 13, wherein the hydrophobic drug is selected from the group consisting of paclitaxel, doxorubicin, cyclosporine.

15. The composition of claim 14, wherein the hydrophobic drug is paclitaxel.

16. The composition of claim 15, wherein said A block polymer is polylactide.

17. The composition of claims 4, wherein the hydrophobic drug is selected from the group consisting of: anti-cancer drugs, antiphlogistic anodynes, immuno-suppressants, hepatism remedies, hormone compositions, chemotherapeutics, metabolic pharmaceuticals, digestive disease remedies, respiratory disease remedies, anti-allergic pharmaceuticals, central nervous system disease remedies, peripheral disease remedies, and circulatory disease remedies.

18. The composition of claim 17, wherein the hydrophobic drug is selected from the group consisting of: paclitaxel, doxorubicin, teniposide, etoposide, daunomycin, methotrexate, mitomycin C, indomethacin, ibuprofen, cyclosporine, and biphenyl dimethyl dicarboxylate(DDB).

19. The composition of claim 18, wherein the hydrophobic drug is selected from the group consisting of paclitaxel, doxorubicin, cyclosporine.

20. The composition of claim 19, wherein the hydrophobic drug is paclitaxel.

21. The composition of claim 20, wherein said A block polymer is polylactide.

22. A method for effectively solubilizing a hydrophobic drug in a hydrophilic environment, comprising the steps of:
   1) preparing a biodegradable polymeric drug carrier micellar solution wherein said micelles consist essentially of a biodegradable amphiphilic block copolymer consisting of BA diblock, ABA triblock and BAB triblock copolymers wherein the B block polymer component is a hydrophilic poly(alkylene oxide) component, and wherein the A block polymer component is a biodegradable hydrophobic polymer component selected from the group consisting of poly(lactic acid), poly(glycolic acid), poly(lactic-co-glycolic acid), and poly(c-caprolactone), wherein the amphiphilic block copolymer has a molecular weight in the range of 1430 to 6000 Daltons and the hydrophilic B block component content is in a range of 50 wt % to 70 wt % based on the total weight of the block copolymer wherein said micelles are composed of a tightly packed hydrophobic polymer core and an outer hydrophilic polymer layer,
   2) mixing a hydrophobic drug with the biodegradable polymeric drug carrier micellar solution; and 3) subjecting the resulted mixture to stirring, heating, ultrasonic treatment, solvent evaporation or dialysis to physically incorporate the hydrophobic drug into the hydrophobic polymer core of the polymeric drug carrier micelle to form a drug containing polymeric micelle composition comprising 70 to 99.999999 percent by weight of the biodegradable polymeric drug carrier and 0.000001 to 30 percent by weight of the hydrophobic drug, and wherein the drug is not covalently bound to the polymeric drug carrier micelle and the resulting drug containing polymeric micelle composition is capable of dissolving in an aqueous solvent carrier to form an aqueous solution.

23. The method of claim 22, wherein said biodegradable polymeric drug containing micelle can be dissolved in said aqueous solution at concentrations of from 0.001 to 40 percent by weight.

24. A method for administering a hydrophobic drug to a warm blooded animal, comprising the steps of:
1) providing a hydrophobic drug solution composition comprising an aqueous solvent carrier containing an effective amount of polymeric micelles which micelles consist essentially of: (a)70 to 99.999999 percent by weight of biodegradable polymeric drug carrier micelles consisting essentially of an amphiphilic block copolymer consisting of BA diblock, ABA triblock and BAB triblock copolymers wherein the B block polymer component is a hydrophilic poly(alkylene oxide) component, and wherein the A block polymer component is a biodegradable hydrophobic polymer component selected from the group consisting of poly(lactic acid), poly(glycolic acid), poly(lactic-co-glycolic acid), and poly($\epsilon$-caprolactone), wherein the amphiphilic block copolymer has a molecular weight in the range of 1430 to 6000 Daltons and the hydrophilic B block component content is in a range of 50 wt % to 70 wt % based on the total weight of the block copolymer wherein said micelles are composed of a tightly packed hydrophobic polymer core and an outer hydrophilic polymer layer; and
(b) 0.000001 to 30 percent by weight of a hydrophobic drug that is physically entrapped within and not covalently bound to said hydrophobic polymer core of said polymeric drug carrier micelles; and
2) administering said drug solution composition to a warm blooded animal.

25. The method of claim 24 wherein said effective amount of polymeric micelles in said aqueous solvent carrier is within a range of about 0.001 to 40% by weight.

26. The method of claim 24, wherein said drug carrier polymeric micelle is a member selected from the group consisting of ABA and BAB triblock copolymers.

27. The method of claim 26, wherein said polymeric drug carrier micelle is an ABA tri-block copolymer.

28. The method of claim 26, wherein B block polymer is monomethoxy poly(alkylene oxide).

29. The method of claim 24, wherein said hydrophilic poly(alkylene oxide) component has an average molecular weight in the range between 1000 to 3300 daltons.

30. The method of claim 24, wherein said A block polymer is polylactide.

31. The method of claims 24, wherein the hydrophobic drug is selected from the group consisting of: anti-cancer drugs, antiphlogistic anodynes, immuno-suppressants, hepatism remedies, hormone compositions, chemotherapeutics, metabolic pharmaceuticals, digestive disease remedies, respiratory disease remedies, anti-allergic pharmaceuticals, central nervous system disease remedies, peripheral disease remedies, and circulatory disease remedies.

32. The method of claim 31, wherein the hydrophobic drug is selected from the group consisting of: paclitaxel, doxorubicin, teniposide, etoposide, daunomycin, methotrexate, mitomycin C, indomethacin, ibuprofen, cyclosporine, and biphenyl dimethyl dicarboxylate(DDB).

33. The method of claim 32, wherein the hydrophobic drug is selected from the group consisting of paclitaxel, doxorubicin, cyclosporine.

34. The method of claim 33, wherein the hydrophobic drug is paclitaxel.

35. The method of claim 33, wherein said A block polymer is polylactide.

36. The method of claims 27, wherein the hydrophobic drug is selected from the group consisting of: anti-cancer drugs, antiphlogistic anodynes, immuno-suppressants, hepatism remedies, hormone compositions, chemotherapeutics, metabolic pharmaceuticals, digestive disease remedies, respiratory disease remedies, anti-allergic pharmaceuticals, central nervous system disease remedies, peripheral disease remedies, and circulatory disease remedies.

37. The method of claim 36, wherein the hydrophobic drug is selected from the group consisting of: paclitaxel, adriamycin, doxorubicin, teniposide, etoposide, daunomycin, methotrexate, mitomycin C, indomethacin, ibuprofen, cyclosporine, and biphenyl dimethyl dicarhoxylate(DDB).

38. The method of claim 37, wherein the hydrophobic drug is selected from the group consisting of paclitaxel, doxorubicin, cyclosporine.

39. The method of claim 38, wherein the hydrophobic drug is paclitaxel.

40. The method of claim 39, wherein said A block polymer is polylactide.

41. The method of claims 28, wherein the hydrophobic drug is selected from the group consisting of: anti-cancer drugs, antiphlogistic anodynes, immuno-suppressants, hepatism remedies, hormone compositions, chemotherapeutics, metabolic pharmaceuticals, digestive disease remedies, respiratory disease remedies, anti-allergic pharmaceuticals, central nervous system disease remedies, peripheral disease remedies, and circulatory disease remedies.

42. The method of claim 41, wherein the hydrophobic drug is selected from the group consisting of: paclitaxel, doxorubicin, teniposide, etoposide, daunomycin, methotrexate, mitomycin C, indomethacin, ibuprofen, cyclosporine, and biphenyl dimethyl dicarboxylate(DDB).

43. The method of claim 42, wherein the hydrophobic drug is selected from the group consisting of paclitaxel, doxorubicin, cyclosporine.

44. The method of claim 43, wherein the hydrophobic drug is paclitaxel.

45. The method of claim 44, wherein said A block polymer is polylactide.

46. The method of claim 24, wherein the administering step being performed by a means selected from the group consisting of oral, parenteral, topical, transdermal and transmucosal administration.

47. The composition of claim 1 wherein said effective amount of polymeric micelles in said aqueous solvent carrier is within a range of about 0.001 to 40% by weight.

* * * * *